United States Patent
Wu et al.

(10) Patent No.: US 10,401,311 B2
(45) Date of Patent: Sep. 3, 2019

(54) METHOD AND DEVICE FOR MEASURING FORMATION ELEMENTAL CAPTURE GAMMA RAY SPECTRA

(71) Applicant: PetroChina Company Limited, Beijing (CN)

(72) Inventors: Hongliang Wu, Beijing (CN); Ning Li, Beijing (CN); Changlin Lan, Beijing (CN); Zhou Feng, Beijing (CN); Qingfu Feng, Beijing (CN); Kewen Wang, Beijing (CN)

(73) Assignee: PetroChina Company Limited, Beijing (CN)

( * ) Notice: Subject to any disclaimer, the term of this patent is extended or adjusted under 35 U.S.C. 154(b) by 0 days.

(21) Appl. No.: 15/888,809

(22) Filed: Feb. 5, 2018

(65) Prior Publication Data
US 2018/0172608 A1 Jun. 21, 2018

Related U.S. Application Data

(63) Continuation of application No. PCT/CN2016/093496, filed on Aug. 5, 2016.

(30) Foreign Application Priority Data

Aug. 6, 2015 (CN) .......................... 2015 1 0477147

(51) Int. Cl.
*G01N 23/222* (2006.01)
*G01N 23/2204* (2018.01)
*G01V 5/10* (2006.01)

(52) U.S. Cl.
CPC ....... *G01N 23/222* (2013.01); *G01N 23/2204* (2013.01); *G01V 5/101* (2013.01)

(58) Field of Classification Search
CPC ..... G01N 23/2204; G01N 23/222; G01V 5/10
See application file for complete search history.

(56) References Cited

U.S. PATENT DOCUMENTS

| | | | |
|---|---|---|---|
| 3,435,215 A | 3/1969 | Pritchett | |
| 5,406,078 A | 4/1995 | Jacobson | |
| (Continued) | | | |

FOREIGN PATENT DOCUMENTS

| | | |
|---|---|---|
| CN | 101906963 | 12/2010 |
| CN | 202256719 | 5/2012 |
| (Continued) | | |

OTHER PUBLICATIONS

"Standard spectrum measurement and simulation of elemental capture spectroscopy log", by Wu Hong-Liang, Li Ning, Lan Chang-Lin, Kong Xiang-Zhong and Chai-Hua, Applied Geophysics, vol. 10, No. 1, dated Mar. 31, 2013, pp. 109-116, 266-276; 10 FIGS; 8 pages.

(Continued)

*Primary Examiner* — Marcus H Taningco
(74) *Attorney, Agent, or Firm* — Faegre Baker Daniels LLP

(57) ABSTRACT

The present invention provides a method and a device for measuring a formation elemental capture gamma ray spectrum, pertaining to the field of oil-gas exploration and well logging technologies. The method comprises: performing moderation on neutrons emitted from a neutron source according to a neutron capture cross section of a test sample; and adjusting a relative location of the test sample with respect to the neutron source, so that a standard capture gamma ray spectrum of the test sample is measured and obtained at a location where a thermal neutron flux reacting with atomic nucleuses of the test sample reaches a first predetermined value. The present invention performs moderation on a neutron source according to neutron capture (Continued)

cross sections of different test samples to measure and obtain elemental capture gamma ray spectra of the test samples, thereby obtaining various formation elemental capture gamma ray spectra with higher accuracy.

10 Claims, 7 Drawing Sheets

(56) References Cited

U.S. PATENT DOCUMENTS

| | | | |
|---|---|---|---|
| 6,124,590 | A | 9/2000 | Mickael |
| 8,217,337 | B2 | 7/2012 | Neville |
| 2002/0175288 | A1* | 11/2002 | Taleyarkhan ........ G01N 23/222 250/358.1 |
| 2003/0225531 | A1* | 12/2003 | Lingren ............. G01N 23/2255 702/23 |
| 2011/0049345 | A1 | 3/2011 | Roberts |
| 2012/0046867 | A1* | 2/2012 | Faber .................... G01T 1/1611 702/8 |

FOREIGN PATENT DOCUMENTS

| | | |
|---|---|---|
| CN | 104237960 | 12/2014 |
| CN | 104297810 | 1/2015 |
| CN | 104329075 | 2/2015 |
| CN | 105093343 | 11/2015 |

OTHER PUBLICATIONS

"Development process and technology prospect of elemental logging based on Gamma ray spectroscopy", by Chao Yuan and Can-can Zhou, Progress in Geophysics at http//www.progeophys.cn; vol. 29, No. 4, dated Dec. 31, 2014, pp. 1867-1872; 6 pages.

First Office Action and Search Report issued by The State Intellectual Property Office of People's Republic of China, dated Jan. 19, 2017, for counterpart Chinese Patent Application No. 2015104771474. 4; 15 pages (including English translation).

Second Office Action and Search Report issued by The State Intellectual Property Office of People's Republic of China, dated Sep. 28, 2017, for counterpart Chinese Patent Application No. 2015104771474.4; 14 pages (including English translation).

International Search Report issued by ISA/CN, dated Sep. 22, 2016, for related International Patent Application No. PCT/CN2016/093496; 3 pages.

Hong-Liang Wu et al: "Standard spectrum measurement and simulation of elemental capture spectroscopy log", Applied Geophysics, vol. 10, No. 1, Mar. 2013 (Mar. 1, 2013), pp. 109-116, XP055361916, Heidelberg ISSN: 1672-7975, DOI: 10.1007/211770-013-0369-1 (8 pages).

European Search Report issued by the European Patent Office, dated Feb. 15, 2019 in related European Application No. 16832345, 4 pages.

\* cited by examiner

METHOD AND DEVICE FOR MEASURING FORMATION ELEMENTAL CAPTURE GAMMA RAY SPECTRA

CROSS-REFERENCE TO RELATED APPLICATIONS

The present application is a continuation of International Application No. PCT/CN2016/093496, filed Aug. 5, 2016, which claims the benefit of Chinese Patent Application No. 201510477147.4, filed Aug. 6, 2015, which are incorporated herein by reference in their entirety.

TECHNICAL FIELD

The present invention relates to a method and device for measuring a formation elemental capture gamma ray spectrum, pertaining to the field of oil-gas exploration and logging technologies.

BACKGROUND

A nuclear logging technology is one of booming cutting-edge logging technologies with the development of contemporary nuclear technologies and the demand of petroleum, coal, geological mineral, or the like for the nuclear logging technology. From the natural gamma ray logging for measuring formation natural radioactivity to the natural gamma ray spectrum logging for calculating contents of uranium, thorium and potassium, to geochemical logging, and then to the current elemental capture spectroscopy (simply referred as ECS) for measuring a thermal neutron capture spectrum of a formation element. The nuclear logging technology provides an effective solution for identifying lithology calculating the skeleton density, determining reservoir physical parameters, researching on sedimentary environment and stratigraphic correlation in a complex reservoir, or the like.

The kernel of the elemental capture spectrum logging interpretation is as below. Firstly, an original measurement spectrum of the formation element is graduated by using a standard spectrum of each element, to obtain a yield of each element by spectrum unfolding. Secondly, the yield of each element is converted to a weight percentage content of each element constituting a formation rock based on an "oxygen closed" theory. Finally, the weight percentage content of the element is converted to that of each mineral by establishing a transformational relation between the formation element and the formation mineral, to implement lithology identification and rock skeleton parameters calculation. However, the key of the elemental capture spectrum logging is how to accurately obtain the standard capture gamma ray spectrum of each element under the simulated logging condition in laboratory, thereby graduating the original measurement spectrum of the stratum, which is the foundation of a complete processing interpretation in elemental capture spectrum logging.

However, in the prior art, there only exists a method for measuring a standard capture gamma ray spectrum of single element such as silicon, calcium, iron, titanium, or the like, and there is a great difference between these spectral lines and the standard data provided by a nuclear database of the international atomic energy agency (IAEA).

SUMMARY

In order to solve the problem of low accuracy existing in the prior method for measuring an elemental capture gamma ray spectrum, the present invention proposes a method and a device for measuring a formation elemental capture gamma ray spectrum, specifically including the following technical solution.

In some embodiments, a method for measuring a formation elemental capture gamma ray spectrum, includes: performing moderation on neutrons emitted from a neutron source according to a neutron capture cross section of a test sample; adjusting a relative position of the test sample with respect to the neutron source, so that a standard capture gamma ray spectrum of the test sample is measured and obtained at a position where a thermal neutron flux reacting with atomic nucleuses of the test sample reaches a first predetermined value.

In some embodiments, a method for measuring a formation elemental capture gamma ray spectrum according to the present invention, the method further includes: performing simulation calculation on the test sample by a predetermined numerical simulation algorithm, and obtaining a simulated measurement result; verifying the measured standard capture gamma ray spectrum and/or the simulated measurement result by nuclear data of the IAEA.

In the method for measuring a formation elemental capture gamma ray spectrum according to the present invention, the performing moderation on neutrons emitted from a neutron source according to a neutron capture cross section of a test sample includes: as for the test sample with a neutron capture cross section greater than a second predetermined value, placing the neutron source in a moderation layer of a first moderation shield, placing a test sample stage at a ray exit of the open first moderation shield, performing moderation and shielding on the neutrons emitted from the neutron source by using the first moderation shield, wherein the test sample stage is used for placing the test sample.

In some variations of the method for measuring a formation elemental capture gamma ray spectrum according to the present invention, the adjusting a relative position of the test sample with respect to the neutron source further includes: adjusting the position of the neutron source located at the front end of a moderation layer by moving the moderation layer in the first moderation shield.

In some variations of the method for measuring a formation elemental capture gamma ray spectrum according to the present invention, the performing moderation on neutrons emitted from a neutron source according to a neutron capture cross section of a test sample includes: as for the test sample with a neutron capture cross section less than the second predetermined value, placing the neutron source at the outer side of a second moderation shield, performing moderation and shielding on the neutrons emitted from the neutron source by using the second moderation shield, wherein the second moderation shield is used for placing the test sample.

In some variations of the method for measuring a formation elemental capture gamma ray spectrum according to the present invention, the adjusting a relative position of the test sample with respect to the neutron source further includes: adjusting a relative position of the test sample with respect to the neutron source by moving the second moderation shield.

In some variations of the method for measuring a formation elemental capture gamma ray spectrum according to the present invention, the measuring and obtaining a standard capture gamma ray spectrum of the test sample includes: measuring and obtaining a background value of gamma ray spectrum at the position where the thermal neutron flux reaches the first predetermined value, and a comprehensive gamma ray spectrum at the position where the thermal neutron flux reaches the first predetermined value; and subtracting the background value of gamma ray spectrum from the comprehensive gamma ray spectrum, to obtain the standard capture gamma ray spectrum of the test sample.

In embodiments of a measuring device for the method for measuring a formation elemental capture gamma ray spectrum according to any of the above-mentioned embodiments the device includes: a measurement body, a first moderation shield, a test sample stage, a detector, a data collecting and processing module and a data analyzing module. The first moderation shield, the test sample stage and the detector are arranged in the measurement body, the first moderation shield is used for carrying the neutron source and performing moderation on the neutrons emitted from the neutron source. The test sample stage is used for placing the test sample, arranged at the ray exit of the first moderation shield. The position of the first moderation shield is moved, so that the detector acquires prompt gamma ray spectrum data of the test sample at a position where the thermal neutron flux reacting with atomic nucleuses of the test sample reaches a first predetermined value, the data collecting and processing module collects and processes the prompt gamma ray spectrum data acquired by the detector, and the data analyzing module analyzes the prompt gamma ray spectrum data and obtains the standard capture gamma ray spectrum of the test sample.

In some variations of the device for measuring a formation elemental capture gamma ray spectrum according to the present invention, the first moderation shield includes a moderation layer, a shield layer and a fixed layer, wherein the moderation layer is used for wrapping the neutron source, the shield layer is wrapped outside the moderation layer, the fixed layer is wrapped outside the shield layer, a Al moderation layer is arranged at the ray exit of the moderation layer, and a shield is arranged outside the first moderation shield at a position corresponding to the detector.

In some variations of the device for measuring a formation elemental capture gamma ray spectrum according to the present invention, a movable structure is adopted between the moderation layer and the shield layer, and the position of the neutron source located at the front end of the moderation layer is adjusted by moving the moderation layer in the first moderation shield.

In some variations of the measuring device for the method for measuring a formation elemental capture gamma ray spectrum according to any of the above-mentioned embodiments the device includes: a measurement body, a second moderation shield, a detector, a data collecting and processing module and a data analyzing module. The second moderation shield and the detector are arranged in the measurement body, the second moderation shield is used for carrying the test sample and performing moderation on the neutrons emitted from the neutron source at the outer side of the second moderation shield. The position of the second moderation shield is moved, so that the detector acquires prompt gamma ray spectrum data of the test sample at a position where the thermal neutron flux reacting with atomic nucleuses of the test sample reaches a first predetermined value, the data collecting and processing module collects and processes the prompt gamma ray spectrum data acquired by the detector, and the data analyzing module analyzes the prompt gamma ray spectrum data and obtains the standard capture gamma ray spectrum of the test sample.

In some variations of the device for measuring a formation elemental capture gamma ray spectrum according to the present invention, the device includes a protecting wall also arranged in the measurement body, for protecting the data collecting and processing module from radiation.

In some variations of the device for measuring a formation elemental capture gamma ray spectrum according to the present invention, metal tungsten is arranged between the neutron source and the second moderation shield, for adjusting the thermal neutron flux of the neutron source reacting with atomic nucleuses of the test sample.

In some variations of the device for measuring a formation elemental capture gamma ray spectrum according to the present invention, the shield layer is arranged at one side of the second moderation shield facing the neutron source.

Advantageously, in various embodiments of the methods and devices of the present invention the moderation is performed on the neutron source for the neutron capture cross sections of different test samples, so as to measure and obtain the elemental capture gamma ray spectrum of the test sample, thereby obtaining various formation elemental capture gamma ray spectra with higher accuracy.

DETAILED DESCRIPTION

In the prior art, no measurement result of the standard capture gamma ray spectrum of various mineral is disclosed under the logging condition. Although some research shows that the measurement schemes and test methods of some elements (such as silicon, calcium and iron) have been established in laboratories, there is a great difference between the spectral lines obtained by these research results and the standard data in the nuclear database of the IAEA. More importantly, the type of neutron source and size parameters of the detector adopted in the existing test devices are greatly different from the parameters of actual subsurface equipment of the elemental capture spectrum logging, by which it is difficult to ensure the measurement accuracy of the capture gamma ray spectrum of each element. Therefore, the present embodiments provide a method for measuring a formation elemental capture gamma ray spectrum which has higher accuracy and is operative, and in view of a small thermal neutron capture cross section of some elements (such as magnesium, potassium, sodium, or the like), the measurement is hardly performed in practice, so the present embodiments further propose a technical solution for mutually verifying the measurement method and the simulated measurement method, thereby obtaining the standard capture gamma ray spectra of ten elements (such as silicon, calcium, iron, or the like) which are accurate and can be used for actual elemental capture spectrum logging and spectrum unfolding calculation.

Figure 1:
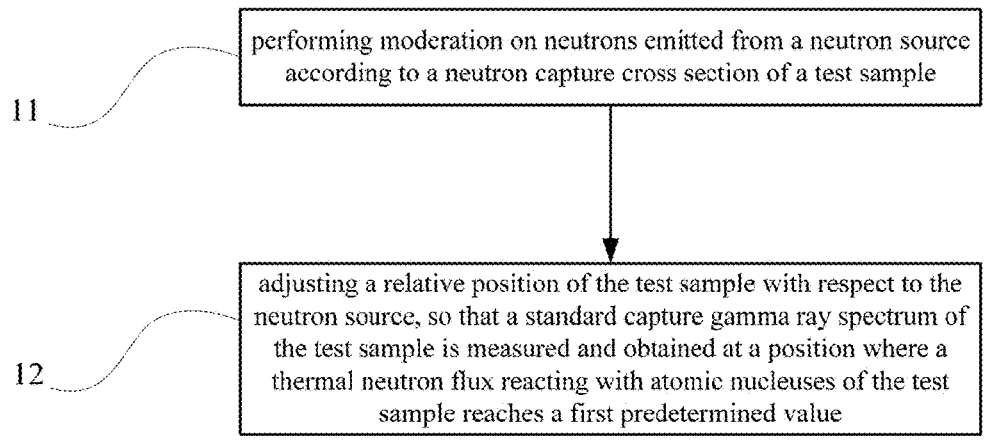
FIG. 1 exemplarily shows a flow chart of a method for measuring a formation elemental capture gamma ray spectrum.

As shown in FIG. 1, the method for measuring a formation elemental capture gamma ray spectrum includes the following steps.

In step 11, moderation is performed on neutrons emitted from a neutron source according to a neutron capture cross section of a test sample.

As for the neutron source, an Am—Be neutron source may be used, and the test samples may be divided into two types according to the size of the neutron capture cross section of the test sample. The first type of elements is the one with a neutron capture cross section greater than the predetermined value, for example, hydrogen, iron, gadolinium, or the like; the second type of elements is the one with a neutron capture cross section less than the predetermined value, for example, magnesium, potassium, sodium, or the like.

In order to obtain better measurement results, by eliminating fast neutrons in the Am—Be neutron source, moderation is performed on the Am—Be neutron source before actual measurements, so that the proportion of the thermal neutrons reacting with the test samples is as large as possible. As for the first type of elements, the moderation may be performed on the Am—Be neutron source, so that the thermal neutron flux onto the test sample after moderation is relatively small; as for the second type of elements, the test sample may be arranged in the moderation shield, so that the thermal neutron flux onto the test sample is relatively large.

In step 12, a relative position of the test sample with respect to the neutron source is adjusted, so that a standard capture gamma ray spectrum of the test sample is measured and obtained at a position where a thermal neutron flux reacting with atomic nucleuses of the test sample reaches a first predetermined value.

In the present application, the implementation order of steps 11 and 12 is not limited. From the point of safety, the relative position of the test sample with respect to the neutron source is firstly adjusted, the adjusted position of the neutron source with respect to the test sample makes the thermal neutron flux reacting with atomic nucleuses of the test sample reach a first predetermined value, and then the neutron source is started.

In implementation, the position of the neutron source with respect to the test sample may be determined by simulation of a Monte Carlo N Particle Transport Code (MCNP) test platform.

In the measuring process, the Am—Be neutron source is placed in the moderation shield, and then the Am—Be neutron source is pushed to the position of the highest thermal neutron flux reacting with an atomic nucleus of the test sample. Finally, the standard capture gamma ray spectrum of the capture thermal neutron of the test sample is measured by a BGO detector.

The method and device for measuring a formation elemental capture gamma ray spectrum will be explained below in detail by specific embodiments.

First Embodiment

Figure 2:
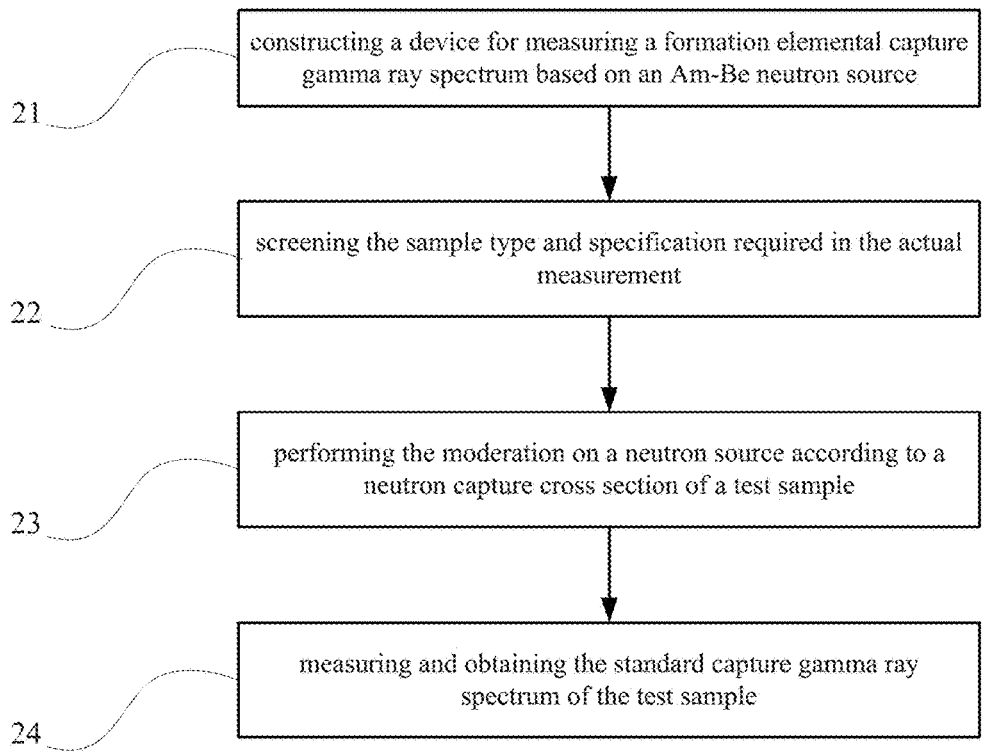
FIG. 2 is a flow chart of a method for measuring a formation elemental capture gamma ray spectrum according to the first embodiment.

As shown in FIG. 2, the method for measuring a formation elemental capture gamma ray spectrum according to the present embodiment includes steps 21-24, described below.

In step 21, a device for measuring a formation elemental capture gamma ray spectrum based on an Am—Be neutron source is constructed.

Figure 3:
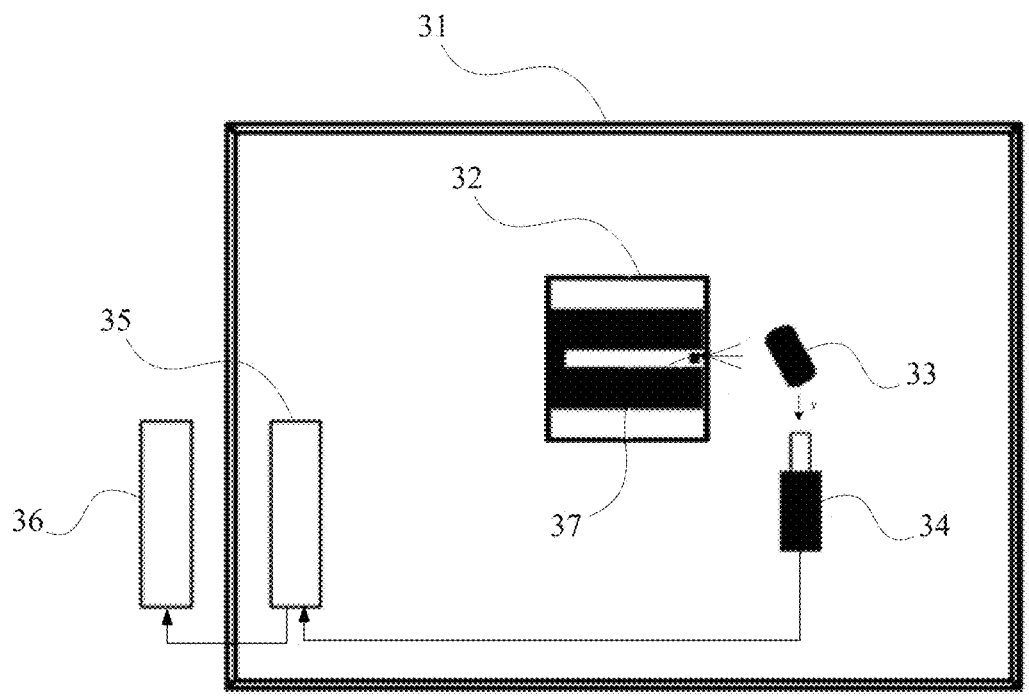
FIG. 3 is a structural diagram of a device for measuring a formation elemental capture gamma ray spectrum according to the first embodiment.

As shown in FIG. 3, the measuring device may include: a measurement body 31, a first moderation shield 32, a test sample stage 33, a detector 34, a data collecting and processing module 35 and a data analyzing module 36. The first moderation shield 32, the test sample stage 33 and the detector 34 are arranged in the measurement body 31, the first moderation shield 32 is used for carrying the neutron source and performing moderation on the fast neutrons emitted from the neutron source 37. The test sample stage 33 is used for placing the test sample, arranged at the ray exit of the first moderation shield 32. The position of the first moderation shield is moved, so that the detector 34 acquires prompt gamma ray spectrum data of the test sample at a position where the thermal neutron flux reacting with atomic nucleuses of the test sample reaches a first predetermined value. The data collecting and processing module 35 collects and processes the prompt gamma ray spectrum data acquired by the detector 34, and the data analyzing module 36 analyzes the prompt gamma ray spectrum data and obtains the standard capture gamma ray spectrum of the test sample.

The device for measuring a formation elemental capture gamma ray spectrum shown in FIG. 3 may be simulated by MCNP, the relative position of the test sample with respect to the neutron source is adjusted by moving the position of the first moderation shield, so that the thermal neutron flux reacting with atomic nucleuses of the test sample reaches the first predetermined value.

As for the neutron source 37, an Am—Be neutron source may be used. The neutron source 37 may be placed in the first moderation shield 32 and used for generating neutron radiation. The first moderation shield 32 is used for performing moderation on the fast neutrons emitted from the Am—Be neutron source and reducing the irradiation dose of neutrons and y to a measurement personnel as much as possible. The test sample stage 33 is arranged at the ray exit of the first moderation shield 32 and is used for placing the test sample. As for the detector 34, a BGO detector (that is, the detector adopting $Bi_4Ge_3O_{12}$ materials) may be used, and is arranged by the side of the test sample stage 33, for collecting the prompt gamma ray spectrum. The data collecting and processing module 35 is connected with the detector 34 by a signal line, for collecting and processing the data collected by the detector 34. The data analyzing module 36 is connected with the data collecting and processing module 35 by a data line, for analyzing the data processed by the data collecting and processing module 35. In this way, the type of neutron source and size parameters of the detector adopted in the measuring device approach the parameters of ECS actual subsurface equipment, thereby providing accuracy of the capture gamma ray spectrum measurement of various elements.

Figure 4:
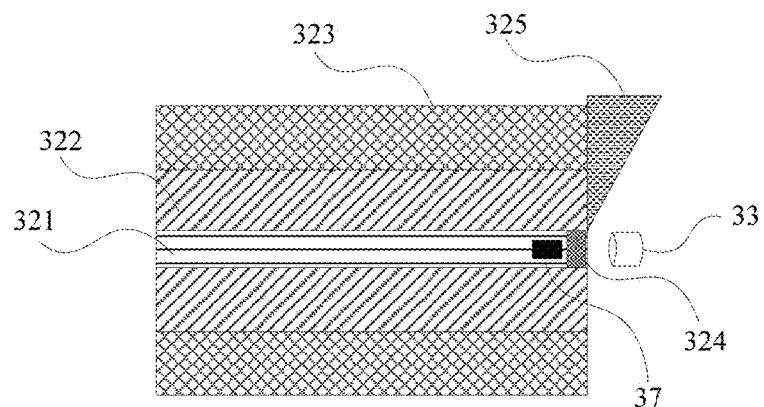
FIG. 4 is another structural diagram of a device for measuring a formation elemental capture gamma ray spectrum according to the first embodiment.

In one optional embodiment, as shown in FIG. 4, the first moderation shield 32 includes a moderation layer 321, a shield layer 322 and a fixed layer 323. The moderation layer 321 is used for wrapping the neutron source 37, the shield layer 322 is wrapped outside the moderation layer 321, the fixed layer 323 is wrapped outside the shield layer 322, a Al moderation layer 324 is arranged at the ray exit of the moderation layer 321, and the shield 325 is arranged outside the first moderation shield 32 at a position corresponding to the detector 34.

The moderation layer 321 can be made of organic glass, the shield layer 322 can be made of polyethylene, the fixed layer 323 has a structure of wrapping a steel plate outside a boron paraffin layer, and the shield 325 has a structure of lead bricks. In order for the measurement personnel to adjust the position of the neutron source 37 conveniently and protect the measurement personnel, a movable design may be adopted between the moderation layer 321 and the shield layer 322. In this way, the measurement personnel may stand at the rear side of the first moderation shield 32, and adjust the position of the neutron source 37 located at the front end of the moderation layer 321 by moving the moderation layer 321, so that the neutron source 37 is pushed to the position of the highest thermal neutron flux reacting with the test sample. In implementation, in order to ensure safety, an electronic control pull mechanism may be further included, fixedly connected with the moderation layer, so that the moderation layer is adjusted afar, thereby adjusting the position of the neutron source.

In step 22, screen out the sample type and specification required in the actual measurement process.

With reference to a condition of selecting a simple substance when each element is measured, screen out the sample specification adopted in the actual measurement process, as shown in Table 1. The test sample with a nuclide of H may be deionized water. The test sample with a nuclide of Na and K may be analytical reagent hydroxide. The test sample with a nuclide of Si, Ca, Mg and Gd may be analytical reagent hydroxide. The test sample with a nuclide of S may be sublimed S simple substance. And the test sample with a nuclide of Ti and Fe may be analytical reagent simple substance.

TABLE 1

| serial number | nuclide | sample | standard |
|---|---|---|---|
| 1 | H | $H_2O$ | deionized water |
| 2 | Na | NaOH | Analytical reagent |
| 3 | Si | $SiO_2$ | Analytical reagent |
| 4 | S | S | sublimed S |
| 5 | Ca | CaO | Analytical reagent |
| 6 | K | KOH | Analytical reagent |
| 7 | Ti | Ti | Analytical reagent |
| 8 | Fe | Fe | Analytical reagent |

TABLE 1-continued

| serial number | nuclide | sample | standard |
|---|---|---|---|
| 9 | Mg | MgO | Analytical reagent |
| 10 | Gd | $Gd_2O_3$ | Analytical reagent |

In step 23, the moderation is performed on the neutron source according to the neutron capture cross section of a test sample.

According to different types of test samples, the measuring device according to the present embodiment is used for measuring the elements with a relatively large neutron capture cross section, such as H, Fe, Gd, or the like. In the actual measurement, the neutron source is placed in the first moderation shield 32, and after the test sample is placed on the test sample stage 33, by moving the position of the first moderation shield 32 (specifically, the first moderation shield may be moved by moving the moderation layer 321), the position of the neutron source 37 placed in the first moderation shield 32 away from the test sample stage 33 is adjusted, and the neutron source 37 is pushed to the position of the highest thermal neutron flux reacting with atomic nucleuses of the test sample. Due to the moderation of the first moderation shield 32 on the neutron source 37, the thermal neutron flux onto the test sample is relatively small, thereby the capturing neutrons in unit time is approximately the same with the element with a relatively small neutron capture cross section, so that the measurement result is closer to the real capture gamma ray spectrum of each element.

In one optional embodiment, the performing moderation on a neutron source according to a neutron capture cross section of the test sample includes: performing moderation and shielding on the neutron source for the test sample with a neutron capture cross section greater than the predetermined value.

Figure 5:
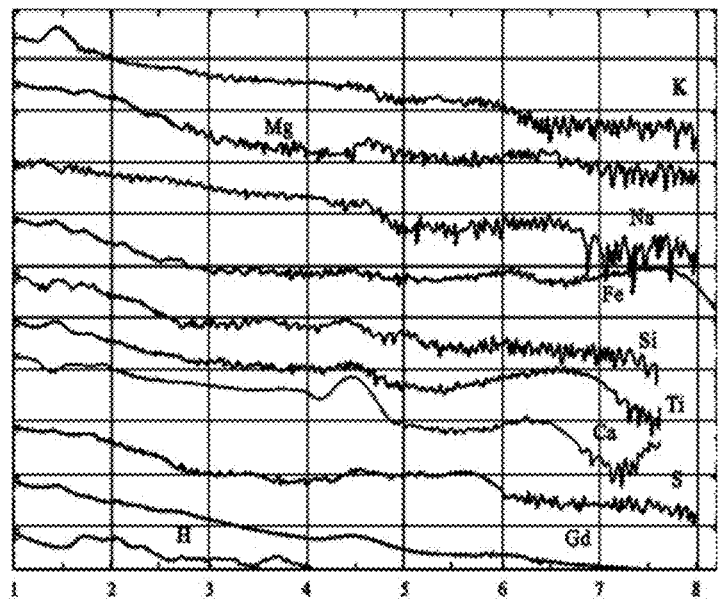
FIG. 5 is a schematic diagram of a result of a measured standard capture gamma ray spectrum of each element according to the first embodiment, wherein the horizontal coordinate represents gamma ray energy in units of MeV, and the vertical coordinate represents a relative counting rate.

Firstly, the simulation calculation is carried out on the neutron field distribution of the spatial region where the measuring device is located. Optionally, the main counting region of the neutron field is a cylindrical region with a geometric center of the test sample stage 33 as a center of a circle, a radius perpendicular to a horizontal plane of 125 cm and a thickness of 5 cm. According to the result of its simulation calculation, it is known that the region with a higher specific value of the thermal neutron flux to the total neutron flux contributes to the arrangement of the test sample to a greater extent. The result of the measured standard capture gamma ray spectrum of each element is as shown in FIG. 5.

In step 24, the standard capture gamma ray spectrum of the test sample is measured.

The measurement personnel collects and processes the prompt gamma ray spectrum data of the test sample acquired by the detector 34 through the data collecting and processing module 35, analyzes the prompt gamma ray spectrum data by the data analyzing module 36, and thus obtains the standard capture gamma ray spectrum of the test sample.

In one optional embodiment, the measuring and obtaining a standard capture gamma ray spectrum of the test sample includes: measuring the background value of the gamma ray spectrum at a position where the thermal neutron flux reaches the first predetermined value, and the comprehensive gamma ray spectrum at a position where the thermal neutron flux reaches the first predetermined value; and subtracting the background value from the comprehensive gamma ray spectrum, to obtain the standard capture gamma ray spectrum of the test sample.

Since the capture gamma ray spectrum of the test sample stage itself may be collected by the detector due to the neutron radiation, the standard capture gamma ray spectrum with higher accuracy of the test sample may be obtained by firstly collecting the background value of the gamma ray spectrum of the test sample stage on which the test sample is not arranged, then collecting the comprehensive gamma ray spectrum of the test sample stage on which the test sample is arranged, and finally subtracting the background value from the comprehensive gamma ray spectrum.

Second Embodiment

Figure 6:
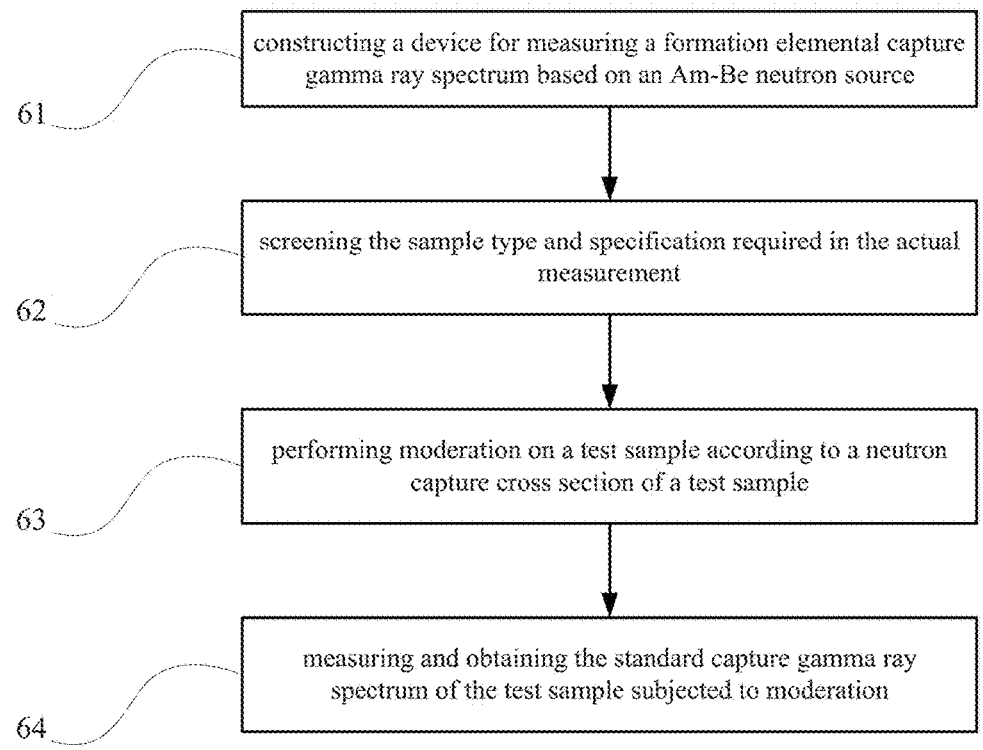
FIG. 6 is a flow chart of a method for measuring a formation elemental capture gamma ray spectrum according to the second embodiment.

As shown in FIG. 6, the method for measuring a formation elemental capture gamma ray spectrum according to the present embodiment includes step 61, constructing a device for measuring a formation elemental capture gamma ray spectrum based on an Am—Be neutron source, and steps 62-64, described below.

Figure 7:
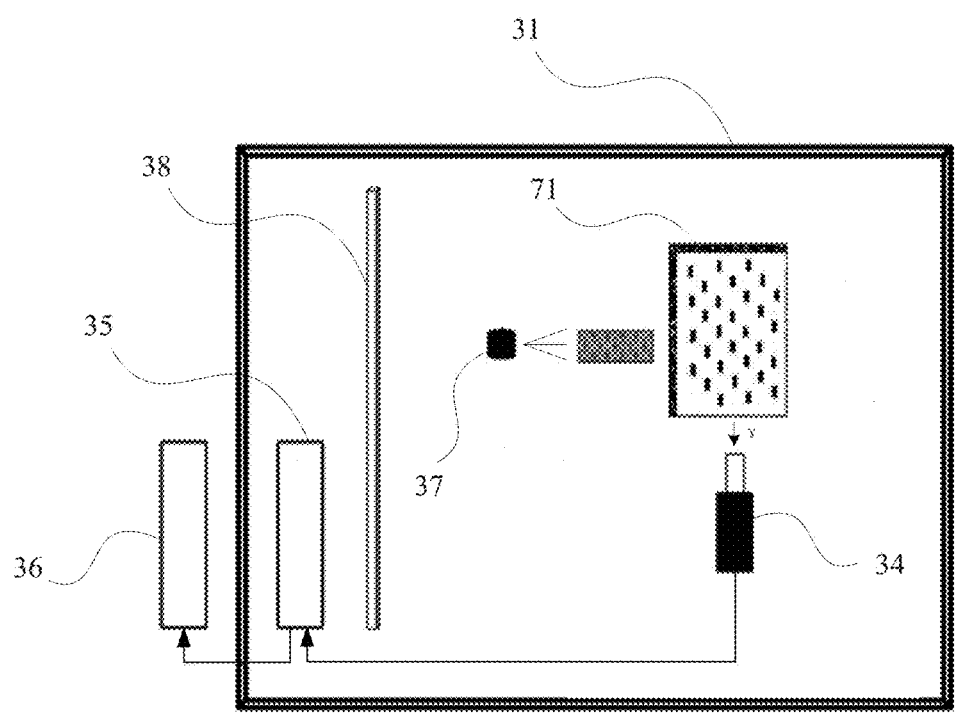
FIG. 7 is a structural diagram of a device for measuring a formation elemental capture gamma ray spectrum according to the second embodiment.

As shown in FIG. 7, the measuring device may include: a measurement body 31, a second moderation shield 71, a detector 34, a data collecting and processing module 35 and a data analyzing module 36. The second moderation shield 71 and the detector 34 are arranged in the measurement body 31. The second moderation shield 71 is used for carrying the test sample and performing moderation on the fast neutrons emitted from the neutron source 37 at the outer side of the second moderation shield, the position of the second moderation shield is moved, so that the detector 34 acquires prompt gamma ray spectrum data of the test sample at a position where the thermal neutron flux reacting with atomic nucleuses of the test sample reaches a first predetermined value. The data collecting and processing module 35 collects and processes the prompt gamma ray spectrum data acquired by the detector 34, and the data analyzing module 36 analyzes the prompt gamma ray spectrum data and obtains the standard capture gamma ray spectrum of the test sample.

As for the neutron source 37, an Am—Be neutron source may be used. The test sample may be arranged in the second moderation shield 71 for performing moderation on the fast neutrons emitted from the neutron source 37 and entering its internal space. The metal tungsten with a predetermined thickness may be arranged between the neutron source 37 and the second moderation shield 71, for adjusting the thermal neutron flux of the neutron source 37 reacting with atomic nucleuses of the test sample, so that the type of neutron source and size parameters of the detector adopted in the measuring device relatively approach the parameters of ECS actual subsurface equipment, thereby improving the accuracy of the capture gamma ray spectrum measurement of each element.

As for the detector 34, a BGO detector may be used and is arranged at the ray exit of the second moderation shield 71, for collecting the prompt gamma ray spectrum. The data collecting and processing module 35 is connected with the detector 34 by a signal line, for collecting and processing data collected by the detector 34. The data analyzing module 36 is connected with the data collecting and processing module 35 by the data line, for analyzing the data processed by the data collecting and processing module 35.

In one optional embodiment, the data collecting and processing module 35 may be also arranged in the measurement body 31. Meanwhile, the protecting wall 38 is also arranged in the measurement body 31, and may be made of paraffin and is used for isolating radioactive rays. The data collecting and processing module 35 is arranged at the rear side of the protecting wall 38, thereby being protected by the protecting wall 38.

In one optional embodiment, the second moderation shield 71 includes a shield layer for carrying the test sample, and the shield layer is made of polyethylene.

In step 62, screen out the sample type and specification required in the actual measurement process.

In the present embodiment, the type and specification of the test sample are screened using the same principle as the first embodiment, and are not repeated herein.

In step 63, the moderation is performed on a test sample according to a neutron capture cross section of a test sample.

According to different types of test samples, the measuring device according to the present embodiment is used for measuring the elements with a relatively small neutron capture cross section, such as Na, Ca, Mg or the like. Since stable simple substances of these elements do not exist in nature, these elements are difficultly measured from compounds and the result has a large error. Therefore, in the present embodiment, only the simple substance element easily acquired or its corresponding oxide or hydroxide is taken as a measurement target.

During the actual measurement, the test sample is placed in the second moderation shield 71, and by moving the position of the second moderation shield 71, the position of the test sample placed in the second moderation shield 71 from the neutron source is adjusted, so that the neutron source 37 reaches the position of the highest thermal neutron flux reacting with atomic nucleuses of the test sample. Since the second moderation shield 71 only performs moderation on the neutrons of the neutron source 37 entering into the second moderation shield 71, the thermal neutron flux onto the test sample is relatively large, thereby the capturing neutrons in unit time is approximately the same with the element with a relatively small neutron capture cross section, so that the measurement result is closer to the real capture gamma ray spectrum of each element.

In step 64, the standard capture gamma ray spectrum of the test sample subjected to moderation is measured and obtained.

The measurement personnel collects and processes the prompt gamma ray spectrum data of the test sample acquired by the detector 34 through the data collecting and processing module 35, analyzes the prompt gamma ray spectrum data by the data analyzing module 36, and thus obtains the standard capture gamma ray spectrum of the test sample.

Third Embodiment

Figure 8:
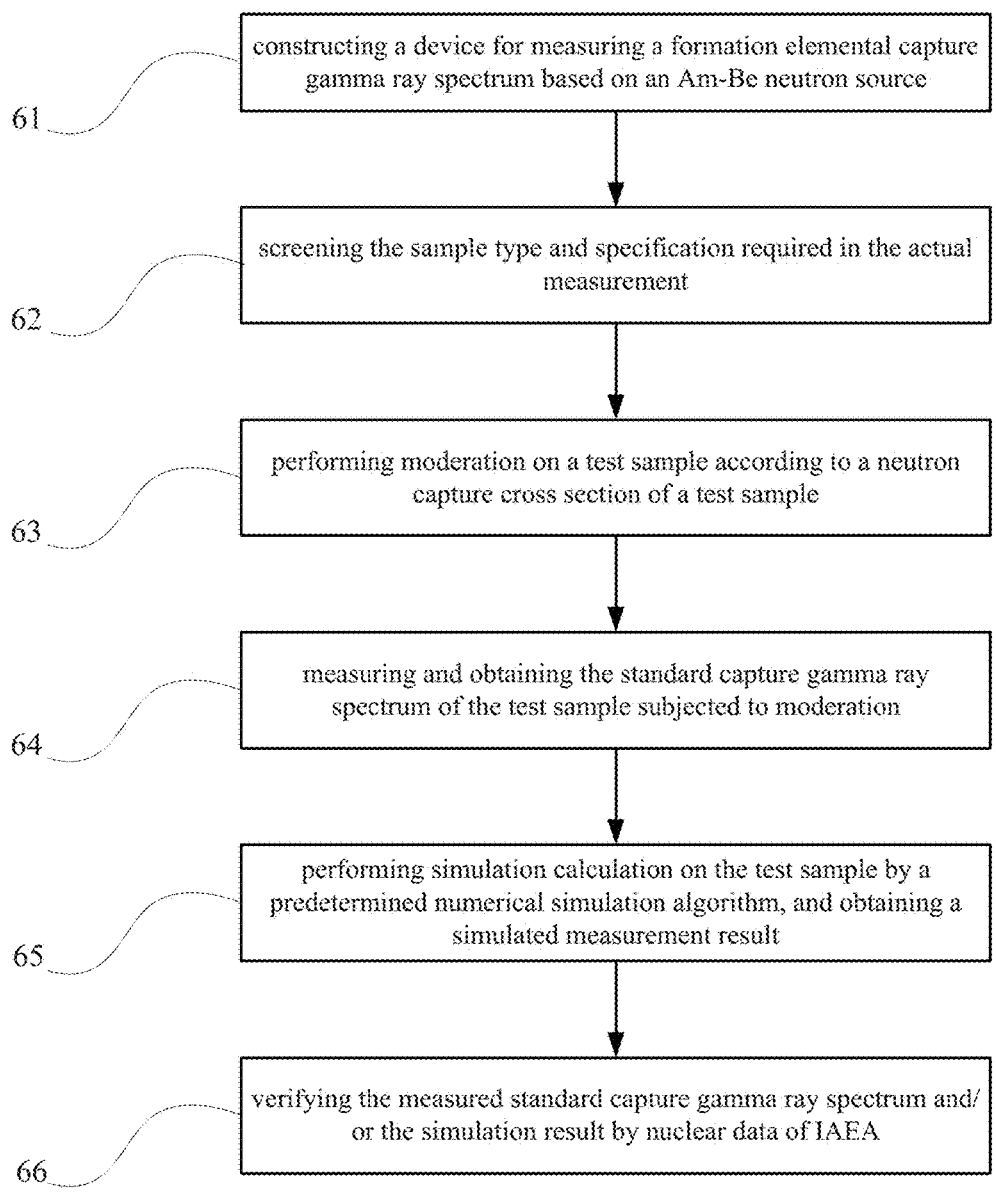
FIG. 8 is a flow chart of a method for measuring a formation elemental capture gamma ray spectrum according to the second embodiment.

As shown in FIG. 8, compared with the second embodiment, the method for measuring a formation elemental capture gamma ray spectrum according to the present embodiment has the same steps 61 to 64, and further includes step 65 and step 66, after step 64.

In step 65, performing simulation calculation on the test sample by a predetermined numerical simulation algorithm, and obtaining a simulated result.

Figure 9:
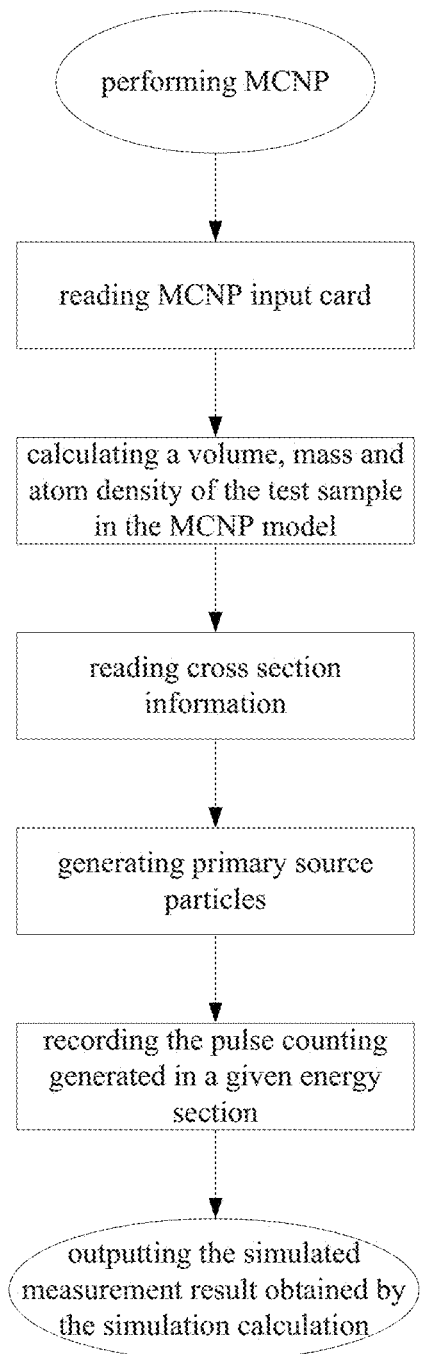
FIG. 9 is a flow chart of a method for performing simulation calculation on the capture gamma ray spectrum of each element by using a numerical simulation method according to the third embodiment.
Figure 10:
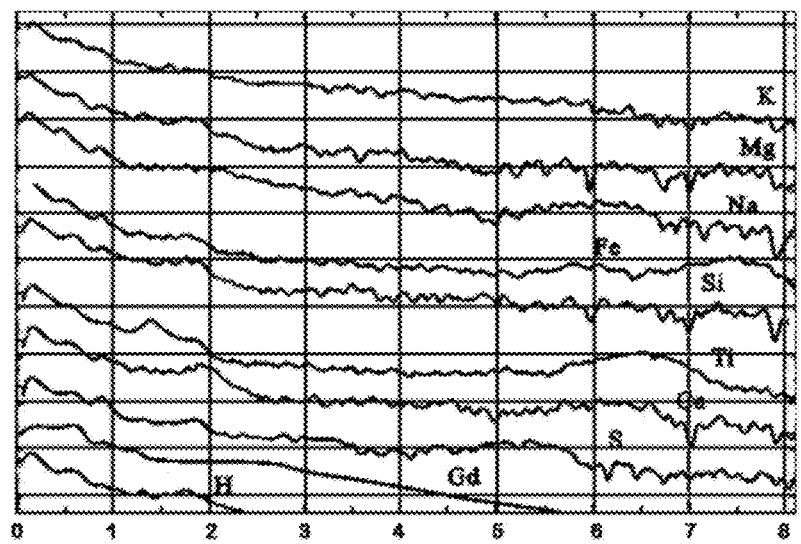
FIG. 10 is a schematic diagram of a simulated result obtained by the numerical simulation algorithm according to the third embodiment, wherein the horizontal coordinate represents gamma ray energy in units of MeV, and the vertical coordinate represents a relative counting rate.

In the case that the same measurement condition and parameters are followed, the method of numerical simulation may be further used to simulate the capture gamma ray spectrum of each element. As shown in FIG. 9, in the present embodiment, during the numerical simulation, the MCNP may be used. The procedure may include: firstly, the content input in an MCNP input card includes the test sample's geometrical input part, a material input part, material interface parameters, a particle transport situation (including a mixed transport of neutrons, photons, electrons), pulse counting or the like; then a volume, mass and atom density of the test sample in the MCNP model are calculated, the cross section information of the test sample is read; the pulse counting generated in a given energy section is recorded according to primary neutron particles generated by simulation; finally, the simulation result is output, and the simulation result obtained by the numerical simulation algorithm is as shown in FIG. 10.

In step 66, the measured standard capture gamma ray spectrum and/or the simulation result is verified by nuclear data of IAEA.

In the present embodiment, the measured standard capture gamma ray spectrum and/or the simulated measurement result is compared with the thermal neutron capture gamma ray energy provided by the nuclear data center of IAEA, thereby verifying the measured standard capture gamma ray spectrum and/or the simulation result. The explanation is given by taking the contrastive analysis of the element of Fe as an example.

Figure 11:
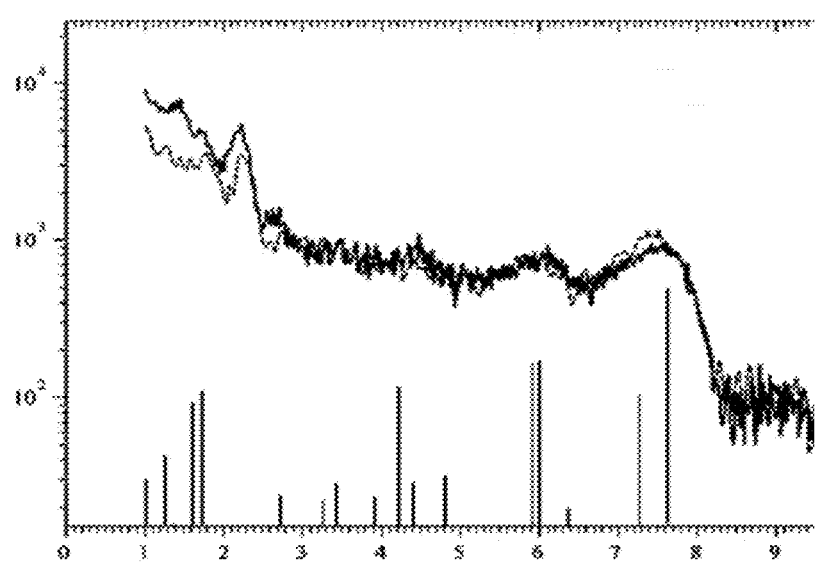
FIG. 11 shows a standard capture gamma ray spectrum obtained by measuring the element of Fe and comparative result of the simulated measurement result with the standard data of the element of Fe in the nuclear data of the IAEA, wherein the horizontal coordinate represents gamma ray energy in units of MeV, and the vertical coordinate represents a relative counting rate.

FIG. 11 shows a standard capture gamma ray spectrum obtained by measuring the element of Fe and comparative result of the simulated measurement result with the standard data of the element of Fe in the nuclear data of IAEA (the vertical coordinate of the nuclear data of IAEA represents the gamma ray intensity with respect to difference energies and is not normalized with the actual measurement counting, without practical comparison meaning.) The solid-line curve in FIG. 11 shows the simulation result, the dashed-line curve represents the measured standard capture gamma ray spectrum, and the black pulse represents the standard data of the element of Fe in the nuclear data of the IAEA. The comparison shows that although the nuclear data provided by the IAEA does not include all the experimental data, but gives a single energy peak of feature gamma ray (that is, a linear spectrum), the measured standard capture gamma ray spectrum and the simulated measurement result has the fluctuation of nuclear electronics, and their peak has an extension. However, they have substantially superimposed energy address where the feature peak is located with the central standard data (for example, the feature peak energy is 6.018 MeV and 7.645 MeV). Therefore, the correctness of the method for measuring a formation elemental capture gamma ray spectrum according to the present embodiment is verified, thereby providing a powerful support for the spectrum unfolding of the original measurement spectrum of the elemental capture energy spectrum.

The method for measuring a formation elemental capture gamma ray spectrum according to the present embodiment has the following advantages: 1) The methods for measuring and simulative-calculating the standard capture gamma ray spectrum of each formation element is established systematically for the first time, and the two methods have good consistency, and can be mutually complemented and verified; 2) the sample type and specification required by each element in the actual measurement are clarified for the first time; 3) based on the actual measurement and monte carlo simulation, the standard and simulated capture gamma ray spectra of 10 elements such as Si, Ca, Fe, or the like are obtained completely for the first time, the actual measurement and simulation results are compared with the thermal neutron capture gamma ray energy in the nuclear data of the IAEA, and the feature gamma ray can be observed, thereby further verifying the correctness of the actual measurement and simulation measurement results, laying the foundation for the further deep research on the elemental capture spectrum logging, and effectively improving the calculation accuracy of spectrum unfolding after the application of the oil field data.

In the present embodiment, the technical solutions of the present invention are clearly and completely described, and the examples are merely part of, instead of all the embodiments of the present invention. Based on the examples in the present invention, any other embodiment obtained by a person skilled in the art without paying any creative effort shall fall within the protection scope of the present invention.

The invention claimed is:

1. A method for measuring a formation elemental capture gamma ray spectrum, comprising:
   performing moderation on neutrons emitted from a neutron source according to a neutron capture cross section of a test sample; and
   adjusting a relative position of the test sample with respect to the neutron source, so that a standard capture gamma ray spectrum of the test sample is measured and obtained at a position where a thermal neutron flux reacting with atomic nucleuses of the test sample reaches a first predetermined value,
   wherein the performing moderation on neutrons emitted from a neutron source according to a neutron capture cross section of a test sample comprises: as for the test sample with a neutron capture cross section greater than a second predetermined value, placing the neutron source in a first moderation shield, placing a test sample stage at a ray exit of the first moderation shield, and performing moderation and shielding on the neutrons emitted from the neutron source by using the first moderation shield, wherein the test sample stage is used for placing the test sample, wherein the first moderation shield comprises a moderation layer, a shield layer and a fixed layer, wherein the moderation layer is used for wrapping the neutron source, the shield layer is wrapped outside the moderation layer, the fixed layer is wrapped outside the shield layer, a Al moderation layer is arranged at the ray exit of the moderation layer, and a shield is arranged outside the first moderation shield at a position corresponding to the detector; and
   wherein the measuring and obtaining a standard capture gamma ray spectrum of the test sample comprises: measuring and obtaining a background gamma ray spectrum at a position where the thermal neutron flux reaches the first predetermined value, and a comprehensive gamma ray spectrum at a position where the thermal neutron flux reaches the first predetermined value; and subtracting the background gamma ray spectrum from the comprehensive gamma ray spectrum, to obtain the standard capture gamma ray spectrum of the test sample.

2. The method according to claim 1, further comprising:
   performing simulation calculation on the test sample by a predetermined numerical simulation algorithm, and obtaining a simulation result; and
   verifying the measured standard capture gamma ray spectrum and/or the simulated measurement result by nuclear data of IAEA.

3. The method according to claim 1, wherein the adjusting a relative position of the test sample with respect to the neutron source further comprises: adjusting the position of the neutron source located at the front end of a moderation layer by moving the moderation layer in the first moderation shield.

4. The method according to claim 1, wherein the performing moderation on neutrons emitted from a neutron source according to a neutron capture cross section of a test sample comprises:

as for the test sample with a neutron capture cross section less than the second predetermined value, placing the neutron source at the outer side of a second moderation shield, performing moderation and shielding on the neutrons emitted from the neutron source by using the second moderation shield, wherein the second moderation shield is used for placing the test sample.

5. The method according to claim 4, wherein the adjusting a relative position of the test sample with respect to the neutron source further comprises: adjusting a relative position of the test sample with respect to the neutron source by moving the position of the second moderation shield.

6. A measuring device for measuring a formation elemental capture gamma ray spectrum, the device comprising: a measurement body, a first moderation shield, a test sample stage, a detector, a data collecting and processing module, and a data analyzing module, wherein the first moderation shield, the test sample stage, and the detector are arranged in the measurement body, wherein the first moderation shield has a ray exit and is used for carrying the neutron source and performing moderation on the neutrons emitted from the neutron source according to a neutron capture cross section of a test sample, wherein the test sample stage is used for placing the test sample, arranged at the ray exit of the first moderation shield, wherein the first moderation shield is movable, so that the detector acquires prompt gamma ray spectrum data of the test sample at a position where the thermal neutron flux reacting with atomic nucleuses of the test sample reaches a first predetermined value, wherein the data collecting and processing module collects and processes the prompt gamma ray spectrum data acquired by the detector, wherein the data analyzing module analyzes the prompt gamma ray spectrum data and obtains the standard capture gamma ray spectrum of the test sample, and wherein the first moderation shield comprises a moderation layer, a shield layer and a fixed layer, wherein the moderation layer is used for wrapping the neutron source, the shield layer is wrapped outside the moderation layer, the fixed layer is wrapped outside the shield layer, a Al moderation layer is arranged at the ray exit of the moderation layer, and a shield is arranged outside the first moderation shield at a position corresponding to the detector.

7. The device according to claim 6, wherein the test sample has a neutron capture cross section greater than a second predetermined value.

8. The device according to claim 7, wherein the second predetermined value is greater than cross sections of magnesium, potassium, and sodium and smaller than cross sections of hydrogen, iron, and gadolinium.

9. The device according to claim 6, wherein the neutron source comprises Am—Be, and the test sample comprises an element selected from hydrogen, iron, and gadolinium.

10. The device according to claim 6, wherein a movable structure is adopted between the moderation layer and the shield layer, and the position of the neutron source located at the front end of the moderation layer is adjusted by moving the moderation layer in the first moderation shield.

* * * * *